United States Patent [19]

Resnick et al.

[11] Patent Number: 5,410,095

[45] Date of Patent: Apr. 25, 1995

[54] PROCESS FOR THE PRODUCTION OF PENTAFLOURODIMETHYL ETHER

[75] Inventors: Paul R. Resnick, Wilmington, Del.; Allen C. Sievert, Elkton, Md.

[73] Assignee: E. I. Du Pont de Nemours and Company, Wilmington, Del.

[21] Appl. No.: 283,309

[22] Filed: Jul. 29, 1994

[51] Int. Cl.$^6$ ............................................. C07C 41/18
[52] U.S. Cl. ..................................................... 568/683
[58] Field of Search ......................................... 568/683

[56] References Cited

FOREIGN PATENT DOCUMENTS

WO94/02564  2/1994  WIPO ............................. C09K 5/04

OTHER PUBLICATIONS

LaZerte, J. D. et al, *Pyroleses of the Salts of Perfluoro Carboxylic Acids*, 75, 4525–4528 (Sep. 20, 1953).
Schack, C. J. et al, *J. of Fluorine Chemistry*, 14, 519–522 (1979).
Berenblit, V. V. et al, "The Nature of the Products of the Electrochemical Fluorination of Ethers of Ethylene Glycol", Trans. from Zhurnal Organicheskoi Khimii, 10 (10), 2031–2035, Oct. 1974.
Berenblit, V. V. et al, "Electrochemical Fluorination of Alkoxycarboxylic Acids", Trans. from Zhurnal Prikladnoi Khimii, 47(11), 2433–2435, Nov., 1974.

*Primary Examiner*—Howard T. Mars

[57] ABSTRACT

A process for the manufacture of pentafluorodimethyl ether is disclosed which involves contacting at least one starting compound selected from the group consisting of compounds having a formula $(CF_3OCF_2CO_2)A$ and compounds having he formula $(CF_3OCF_2CO_2)_2A'$ wherein A is selected from the group consisting of hydrogen, ammonium, alkali metals (e.g., sodium or potassium) and R (wherein R is a $C_1$ to $C_4$ alkyl group) and A' is an selected from the group consisting of alkaline-earth metals (e.g., magnesium or calcium), with at least one hydroxylic compound selected from the group consisting of water, mono-alcohols of the formula R'OH (wherein R' is a $C_1$ to $C_{12}$ straight or branched chain alkyl group) and alkanediols of the formula $R''(OH)_2$ (wherein R'' is a $C_2$ to $C_8$ alkylene group) at temperature of about 120° C. to 170° C.

8 Claims, No Drawings

PROCESS FOR THE PRODUCTION OF PENTAFLOURODIMETHYL ETHER

FIELD OF THE INVENTION

This invention relates to processes for the manufacture of ethers containing fluorine, and more particularly processes for the production of pentafluorodimethyl ether.

BACKGROUND

Chlorofluorocarbons (i.e., compounds containing only carbon, fluorine and chlorine) have been used for many years as refrigerants, heat transfer media, foam expansion agents, aerosol propellants, solvents and power cycle working fluids. However, there has been recent concern that chlorofluorocarbons might be detrimental to the Earth's ozone layer. Consequently, there is a worldwide effort to find alternative compounds which contain fewer chlorine substituents, preferably compounds containing no chlorine. Pentafluorodimethyl ether has been proposed as a replacement for some CFCs (see e.g., PCT Publication No. WO 94/02564). Thus, there is an interest in pentafluorodimethyl ether, and a need for an efficent process for its production.

SUMMARY OF THE INVENTION

This invention provides a process for the manufacture of pentafluorodimethyl ether (i.e., $CHF_2OCF_3$) comprising the step of contacting at least one starting compound selected from the group consisting of compounds having a formula $(CF_3OCF_2CO_2)A$ and compounds having the formula $(CF_3OCF_2CO_2)_2A'$ wherein A is selected from the group consisting of hydrogen, ammonium, alkali metals (e.g., sodium or potassium) and R (wherein R is a $C_1$ to $C_4$ alkyl group) and A' is selected from the group consisting of alkaline-earth metals (e.g., magnesium or calcium), with at least one hydroxylic compound selected from the group consisting of water, mono-alcohols of the formula R'OH (wherein R' is a $C_1$ to $C_{12}$ straight or branched chain alkyl group) and alkanediols of the formula R"(OH)$_2$ (wherein R" is a $C_2$ to $C_8$ alkylene group) at a temperature of about 120° C. to 170° C.

DETAILED DESCRIPTION

In accordance with this invention $CHF_2OCF_3$ may be produced from compounds of the formula $CF_3OCF_2CO_2A$, where A is selected from the group consisting of hydrogen, ammonium, alkali metals (e.g., sodium and/or potassium) and $C_1$ to $C_4$ alkyl group (i.e., R). The sodium and potassium salts of $CF_3OCF_2CO_2H$ are known compounds and can be prepared by hydrolysis of the corresponding acid fluoride, $CF_3OCF_2C(O)F$, in the presence of sodium or potassium hydroxide. The acid fluoride, $CF_3OCF_2C(O)F$, may be prepared by electrochemical fluorination of $CH_3OCH_2CO_2H$ as described by Berenblit, et al. in Zhurnal Prikladnoi Khimii, Vol. 47, pp. 2433–2435 (1974). Alternatively, $CF_3OCF_2C(O)F$ may be prepared by reaction of cesium fluoride with $CF_3OCF_2CF_2OSO_2F$ as described by Schack et al. in Journal of Fluorine Chemistry, Vol. 14, pp. 519–522 (1979). Perfluoromethoxyacetic acid is a known compound and can be prepared by acidification of the salts. Esters of the acid, $CF_3OCF_2CO_2R$, wherein R is a $C_1$ to $C_4$ alkyl group, can be prepared by standard esterification methods (e.g., acid catalyzed reaction of $CF_3OCF_2CO_2H$ with $C_1$ to $C_4$ alcohols).

$CHF_2OCF_3$ may also be provided in accordance with this invention from compounds of the formula $(CF_3OCF_2CO_2)_2A'$ where A' is selected from the group consisting of alkaline-earth metals (e.g., magnesium and/or calcium). These alkaline-earth metal salts can be prepared by hydrolysis of the corresponding acid fluoride, $CF_3OCF_2C(O)F$, in the presence of a soluble salt (e.g., magnesium or calcium chloride).

In accordance with this invention, the $CF_3OCF_2CO_2A$ and/or $(CF_3OCF_2CO_2)_2A'$ reactant is reacted with a hydroxylic compound. Suitable hydroxylic compounds for the process of the invention include water, mono-alcohols, R'OH, where R' is a $C_1$ to $C_{12}$ straight or branched chain alkyl group, and alkanediols, R"(OH)$_2$, where R" is a $C_2$ to $C_8$ alkylene group. Mixtures of water, monoalcohols, and alkanediols may also be used. Examples of mono-alcohols suitable for the process of the invent ion include n-propanol, isopropanol, and n-butanol; examples of alkanediols suitable for the process of the invention include ethylene glycol, diethylene glycol, 1,2-propanediol, and 1,4-butanediol. The choice of hydroxylic compound or compounds chosen for the process of the invention depends on the mode of the reaction employed; that is, whether it is operated in a batch or continuous mode, the solubility of the perfluoromethoxyacetic acid derivative chosen, and whether the process is to be run at atmospheric or higher pressure.

The amount of hydroxyl group should be at least a stoichiometric amount with respect to the perfluoromethoxyacetic acid derivative. Generally, the molar ratio of hydroxyl group to the perfluoromethoxyacetic acid derivative can range from about 1:1 to about 2000:1 and preferably about 10:1 to 1500:1.

The reaction of $CF_3OCF_2CO_2A$ and/or $(CF_3OCF_2CO_2)_2A'$ with a hydroxyl compound is suitably conducted at a temperature in the range of from about 120° C. to about 170° C., preferably from about 140° C. to about 170° C., and more preferably from about 150° C. to about 160° C. Suprisingly, we find that it is possible to conduct the process of the invention on mixtures of $CF_3OCF_2CO_2A$ and/or $(CF_3OCF_2CO_2)_2A'$ containing other perfluorocarboxylic acid salts (e.g., $CF_3CO_2A$, $CF_3CF_2CO_2A$, $(CF_3O_2)_2A'$ and $(CF_3CF_2CO_2)_2A'$ wherein A and A' are as defined above) and other fluoride salts so that $CF_3OCHF_2$ is obtained selectively with little contamination from other decarboxylation products such as $CHF_3$ and $C_2HF_5$ as illustrated in Example 2 below (i.e., the starting compound of this invention is selectivily decarboxylated when compared to said other perfluorocarboxylic acid salts in the mixture). Such surprising selectivity in the decarboxylation reaction may be obtained by operating the reaction within the more preferred temperature range as defined above. Operating the decarboxylation at higher temperatures can result in either increasing the amounts of other decarboxylation by-products or lowering the yield of the desired $CF_3OCHF_2$. Preferably, the reaction variables (e.g., time and temperature) are selected such that the mole ratio of $CHF_3$ to $CF_3OCHF_2$ in the reaction product is less than about 1:5, more preferably less than about 1:19.

The process of the invention may be conducted in either a batch or continuous mode. In batch mode, the perfluoromethoxyacetic acid derivative is combined with water or alcohol or mixture thereof in a suitable reaction vessel. Suitable reaction vessels include glass reactors or steel autoclaves. The mixture is then heated to the desired temperature for a suitable period of time. If the reaction is capable of withstanding pressure, the gaseous products may be retained in the reactor. Alternatively, the products may be removed from the reactor as they are formed. The products are then collected and separated by conventional techniques, such as by condensation and distillation. If the reaction is conducted in a batch mode and the products are retained in the reactor, then the temperature of the reaction must be low enough that the desired product, $CF_3OCHF_2$, is stable as illustrated by the Comparative Examples below.

In continuous mode, perfluoromethoxyacetic acid derivative, or a solution thereof in a suitable solvent such as water, alcohol, or mixture thereof, is added to a reactor pre-heated to the desired reaction temperature. Gaseous products are removed as they are formed. The reactor can consist of a glass or steel reaction vessel such as an autoclave containing a suitable solvent or solvent mixture, or the reaction vessel may be of tubular design.

Since carbon dioxide is a by-product of the reaction, it is convenient to remove this from the product mixture by passing said mixture through a basic scrubber such as solid soda lime or an aqueous caustic solution.

The half-life of the perfluoromethoxyacetic acid derivative is temperature dependent. Therefore, the reaction time is dependent on the reaction temperature employed. In batch mode, reaction times are normally from about 10 to about 180 minutes, preferably from about 20 to about 120 minutes.

The rate of the reaction is pH dependent. Generally, the higher the pH, the faster is the reaction rate. A pH of at least about 7 is preferred. If desired, the pH of the solvent mixture as defined above can be adjusted to at least 7 with a suitable base, such as sodium or potassium hydroxide.

Pressure is not critical. Atmospheric and superatmospheric pressures (e.g., pressures from about 100 kPa to 7000 kPa) are the most convenient and are therefore preferred. If the solvent system is entirely aqueous, then the process of the invention must be conducted under pressure to attain the desired reaction temperature. Use of a suitable alcohol, as defined above, or mixture of alcohol and water, can allow the process to be run at atmospheric pressure. A suitable alcohol or mixture of alcohol and water would be one having a normal boiling point at least equal to the desired reaction temperature.

Practice of the invention will become further apparent from the following nonlimiting examples.

EXAMPLE 1

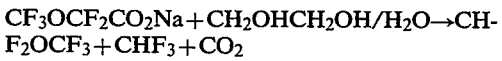

A 2-L 4-necked flask was equipped with a mechanical stirrer, a thermometer, an addition funnel, and a condenser cooled with ethylene glycol/water to about 5° C. The exit side of the condenser was connected to two soda lime scrubbers in series followed by two one-liter collection cylinders immersed in dry-ice baths; the last cylinder was connected to a nitrogen bubbler.

The flask was charged with ethylene glycol (800 mL) and the addition funnel was charged with a mixture of sodium perfluoromethoxyacetate (240.4 g, 1.19 mole), ethylene glycol (360 mL) and water (9 mL). The flask was warmed to 140° C. and addition of the sodium perfluoromethoxyacetate begun. A slight exotherm increased the temperature to about 150° C. Addition of the sodium salt was done at 149°–152° C. over 6.3 hours.

Product (113.1 g) was covered in the first collection cylinder. GC analysis of the product showed that it contained 96.5 GC area percent $CHF_2OCF_3$ and 3.2% $CHF_3$.

EXAMPLE 2

An aqueous process stream was analyzed and found to contain about 2.35% by weight $CF_3OCF_2COOK$, about 3.76% by weight $CF_3COOK$, about 9.58% by weight KF, about 0.34% by weight $CF_3CF_2COOK$ and about 0.38% by weight $CF_3C(OH)_2COOK$. The pH of the stream was about 10.0. A 282.8 g sample of this material was heated in a Hastelloy ® nickel alloy tube at 150° C. for 5 hours. The gaseous products were condensed in a −78° C. trap to give 4.69 of a colorless liquid. IR and NMR analyses showed it be a mixture of about 88 mole percent $CF_3OCF_2H$ and about 12 mole percent $CHF_3$. The yield of $CF_3OCF_2H$ was approximately 100% based upon the starting materials of this invention.

The liquid remaining in the tube weighed 271.2 g. The $^{19}F$ NMR analysis of this liquid showed the presence of $CF_3COOK$, KF and $CF_3CF_2COOK$ as the only fluorine containing species.

| Material | Mole Ratio Starting Material | Mole Ratio Liquid Product | % Remaining |
|---|---|---|---|
| $CF_3COOK$ | 0.152 | 0.128 | 84 |
| $CF_3CF_2COOK$ | 0.011 | 0.0084 | 76 |
| KF | 1.000 | 1.000 | 100 |
| $CF_3OCF_2COOK$ | 0.0655 | 0.000 | 0 |
| $CF_3C(OH)_2COOK$ | 0.0182 | 0.000 | 0 |

EXAMPLE 3

A 2800 g sample of a aqueous stream of pH 10.36 containing about 2.41% by weight $CF_3OCF_2COOK$, about 3.13% by weight $CF_3COOK$, about 7.79% by weight KF, about 0.53% by weight $CF_3CF_2COOK$ and about 0.71% by weight $CF_3C(OH)_2COOK$ was heated in a stainless steel autoclave at 150° C. for 2 hours. The gaseous products were bled through a KOH scrubber, Drierite ® drying tower and condensed in a −78° C. trap to give 19.4 g of colorless liquid which was almost all $CF_3OCF_2H$. The yield was about 46%. The liquid product weighed 2742 g and had a pH of about 9.28. $^{19}F$ NMR analyses of the starting material and product showed:

| Component | Starting Material | Product | % Change |
|---|---|---|---|
| $CF_3OCF_2COOK$ | 67.48 g | 5.30 g | −92.1 |
| $CF_3COOK$ | 87.64 | 92.05 | +5.0 |
| KF | 218.12 | 267.72 | +22.7 |
| $CF_3C(OH)_2COOK$ | 19.88 | 0 | −100.0 |
| $CF_3CF_2COOK$ | 14.84 | 14.73 | −0.7 |

EXAMPLE 4

A 240 mL Hastelloy ™ C nickel alloy shaker tube was charged with sodium perfluoromethoxyacetate (40 g, 0.20 mole) and 100 g of n-propanol. The tube was sealed, cooled in dry ice, and purged with nitrogen. The tube was then heated to 150° C. for 5 hours; during this time the pressure rose to 636 psig (4485 kPa). After cooling, the vapor phase was transferred to a cylinder (weight recovered, about 16 g). The tube was discharged to give 112.1 g of a clear supernatant over a flocculent white solid. The solid after filtration and air-drying weighed 9.3 g. Analysis of the vapor phase from the reactor by GC and GC-MS indicated that pentafluorodimethyl ether was the major component along with nitrogen, carbon dioxide as well as propanol and other unidentified higher boiling materials; no trifluoromethane was detected.

COMPARATIVE EXAMPLE 1

An aqueous process stream having a pH of about 10.0 was analyzed and found to contain about 2.35 weight percent $CF_3OCF_2COOK$, about 3.76 weight percent $CF_3COOK$, 9.58 weight percent KF, about 0.34 weight percent $CF_3CF_2COOK$ and about 0.38 weight percent $CF_3C(OH)_2COOK$. The aqueous process stream was allowed to react under various conditions as summarized in the following table.

| Run | Temp. | Time | Press. | pH | Comments |
|---|---|---|---|---|---|
| 1 | 200° C. | 3 h | Autog. | 9–10 | |
| 2 | 150 | 6 | Autog. | 9–10 | |
|   | 200 | 3 | | | |
| 3 | 200 | 3 | Autog. | 9–10 | KOH Added to Feed |
| 4 | 100 | 18.3 | Atm. | | No Reaction |
| 5 | 200 | 3 | Autog. | 7.0 (initial) 9–10 (final) | |

The runs are further discussed below.

RUN 1

A 200 mL sample of the aqueous process shown was heated in a Hastelloy ® nickel alloy tube at 200° C. for 3 hours. The tube had positive pressure after cooling to room temperature. The gases were sampled and found to contain carbon dioxide, $CHF_3$ and $CF_3CF_2H$ using infrared, $^{19}F$ NMR and $^1H$ NMR analyses. The $^{19}F$ NMR analysis of the aqueous liquid showed the presence of fluoride ion. There were no other fluorine resonances observed.

RUN 2

A 200 mL sample of the same aqueous stream was heated in a Hastelloy ® nickel alloy tube at 150° C. for 6 hours and at 200° C. for 3 hours. The gaseous products were shown by IR and NMR analyses to contain carbon dioxide, $CHF_3$ and $CF_3CF_2H$. No $CF_3OCF_2H$ was observed. The pH of the aqueous residue from the reaction was from about 9 to 10. Fluoride ion and a trace of $CHF_3$ were the only fluorine resonances observed in the $^{19}F$ NMR spectrum of this residue.

RUN 3

A 200 mL sample of the same aqueous stream and 2 g potassium hydroxide were heated at 200° C. for 3 hours. The gaseous products were shown by IR and NMR analyses to contain $CHF_3$ and $CF_3CF_2H$. No $CF_3OCF_2H$ was observed. The pH of the aqueous residue from the reaction was from about 9 to 10. Fluoride ion and a trace of $CHF_3$ were the only fluorine resonances observed in the $^{19}F$ NMR spectrum of this residue.

RUN 4

A 100 mL sample of the same aqueous stream was heated to 100° C. at atmospheric pressure for 18.25 hours in a round bottom flask topped by a water cooled condenser and Dry Ice cooled trap. There was no material in the Dry Ice cooled trap. The $^{19}F$ NMR spectrum of the liquid product showed no change in KF, $CF_3OCF_2COOK$, $CF_3COOK$, and $CF_3CF_2COOK$. No $CF_3C(OH)_2COOK$ remained.

RUN 5

A 210 g sample of the same aqueous stream which had been neutralized to a pH of about 7.03 with aqueous sulfuric acid was heated in a Hastelloy ® nickel alloy tube at 200° C. for 3 hours. The gaseous products were shown by IR and NMR analyses to contain carbon dioxide, $CHF_3$ and $CF_3CF_2H$. No $CF_3OCF_2H$ was observed. The pH of the aqueous residue from the reaction was from about 9 to 10. Fluoride ion and HF were the only fluorine resonances observed in the $^{19}F$ NMR spectrum of this residue.

COMPARATIVE EXAMPLE 2

A mixture of 200 mL water, 13.2 g 85% KOH and 4.79 g $CF_3OCF_2H$ was heated in a Hastelloy ® tube at 200° C. for 6 hours. The volatile material contained carbon dioxide, $CHF_3$ and a minute trace of another fluorine containing material. The liquid residue, 205.6 g had a pH of about 9 and contained about 4.09% by weight KF. No starting $CF_3OCF_2H$ was found.

COMPARATIVE EXAMPLE 3

A mixture of 6.1 g $CF_3OCF_2COONa$, 200 mL water and 1.0 g NaOH was heated in a Hastelloy ® nickel alloy tube at 200° C. for 3 hours. The volatile products contained $CF_3OCF_2H$ and $CHF_3$ in a mole ratio of 1:10. The residue was 195.2 g of a colorless liquid with a pH of about 5 which contained HF as well as fluoride and bifluoride along with a trace of $CHF_3$.

What is claimed is:

1. A process for the manufacture of pentafluorodimethyl ether comprising the step of:
    contacting at least one starting compound comprising a perfluoromethoxyacetic acid derivative selected from the group consisting of compounds having a formula $(CF_3OCF_2CO_2)A$ and compounds having the formula $(CF_3OCF_2CO_2)_2A'$ wherein A is selected from the group consisting of hydrogen, ammonium, alkali metals, and R, wherein R is a $C_1$ to $C_4$ alkyl group, and A' is an selected from the group consisting of alkaline-earth metals, with at least one hydroxylic compound selected from the group consisting of water, mono-alcohols of the formula R'OH wherein R' is a $C_1$ to $C_{12}$ straight or branched chain alkyl group, and alkanediols of the formula R" $(OH)_2$, wherein R" is a $C_2$ to $C_8$ alkylene group, at a temperature of about 120° C. to 170° C.

2. The process of claim 1 wherein the pH is at least about 7.

3. The process of claim 2 wherein the temperature is from about 140° C. to 170° C.

4. The process of claim 2 wherein the process is conducted in a batch mode and the reaction time is from about 10 to 180 minutes.

5. The process of claim 4 wherein the time and temperature are selected such that the mole ratio of $CHF_3$ to $CF_3OCHF_2$ in the reaction product is less than about 1:5.

6. The process of claim 2 wherein the process is conducted in a continuous mode.

7. The process of claim 6 wherein the time and temperature are selected such that the mole ratio of $CHF_3$ to $CF_3OCHF_2$ in the reaction product is less than about 1:5.

8. The process of claim 2 wherein the perfluoromethoxyacetic acid derivative is contained in a mixture which also contains at least one other perfluorocarboxylic acid salt selected from the group consisting of $CF_3CO_2A$, $CF_3CF_2CF_2A$, $(CF_3CO_2)_2A'$ and $(CF_3CF_3CO_2)_2A'$, and the perfluoromethoxyacetic acid derivative is selectively decarboxylated when compared to said other perfluorocarboxylic acid salts in the mixture.

* * * * *